(12) United States Patent
Stauch

(10) Patent No.: US 8,252,063 B2
(45) Date of Patent: Aug. 28, 2012

(54) GROWING PROSTHESIS

(75) Inventor: Roman Stauch, Assamstadt (DE)

(73) Assignee: Wittenstein AG, Igersheim (DE)

(*) Notice: Subject to any disclaimer, the term of this patent is extended or adjusted under 35 U.S.C. 154(b) by 183 days.

(21) Appl. No.: 12/716,303

(22) Filed: Mar. 3, 2010

(65) Prior Publication Data

US 2010/0228357 A1  Sep. 9, 2010

(30) Foreign Application Priority Data

Mar. 4, 2009 (DE) .......................... 10 2009 011 661

(51) Int. Cl.
*A61F 2/28* (2006.01)
*A61F 2/30* (2006.01)
(52) U.S. Cl. ................... 623/23.47; 623/23.45; 606/62; 606/63
(58) Field of Classification Search ............... 623/23.45, 623/23.47; 606/62, 63, 90
See application file for complete search history.

(56) References Cited

U.S. PATENT DOCUMENTS

| 6,416,516 | B1 | 7/2002 | Stauch et al. | |
|---|---|---|---|---|
| 2004/0030395 | A1* | 2/2004 | Blunn et al. | 623/18.12 |
| 2006/0004459 | A1* | 1/2006 | Hazebrouck et al. | 623/18.12 |
| 2006/0069447 | A1* | 3/2006 | DiSilvestro et al. | 623/23.16 |

FOREIGN PATENT DOCUMENTS

| DE | 19906423 | | 8/2000 |
|---|---|---|---|
| EP | 0776432 | | 6/1997 |
| EP | 1371346 | | 12/2003 |
| EP | 1371346 | A1 * | 12/2003 |

* cited by examiner

*Primary Examiner* — David H Willse
*Assistant Examiner* — Javier Blanco
(74) *Attorney, Agent, or Firm* — Bachman & LaPointe, P.C.

(57) ABSTRACT

A growing prosthesis comprising a joint replacement part, a prosthesis stem, a stem-anchoring element, and an element with corresponding drive provided for the lengthening of the growing prosthesis. The element provided for the lengthening of the growing prosthesis is a spindle element arranged in the stem-anchoring element.

8 Claims, 3 Drawing Sheets

GROWING PROSTHESIS

BACKGROUND OF THE INVENTION

The invention relates to a growing prosthesis comprising a bone prosthesis, in particular a joint replacement part, a prosthesis stem, a stem-anchoring element, and an element with corresponding drive provided for the lengthening of the growing prosthesis.

A number of growing prostheses are known from the prior art.

Growing prostheses in most cases consist of a lengthenable prosthesis part and of a stem-anchoring element, which is fixed in the bone. In devices of this kind, an electric drive is located in the prosthesis part. Spindle roller systems are mostly used as the electric drive. A drive unit of this kind is disclosed in EP 0 776 432 B1. The device converts a rotary movement into an axial movement using planetary rollers, which are driven by a drive shaft out of a stationary drive housing and held peripherally at uniform spacings, and a pusher body that can be axially displaced by the planetary rollers.

On account of the movement of the drive unit, the telescopic element of the prosthesis is moved out and the prosthesis is lengthened. The stem-anchoring element can have different lengths and cross sections and can be of modular construction, such that it can be adapted to the different medullary cavity dimensions.

EP 1 371 346 B1 discloses, for example, an implantable prosthesis for replacement of the human hip joint or knee joint and of the adjacent portions of the diaphysis, wherein the prosthesis has a joint part, a stem-anchoring part and, arranged between the joint part and the stem-anchoring part, a stem replacement part. The stem replacement part and the artificial joint each have a continuous central bore, said bores being aligned with each other. The stem-anchoring part is formed in the present invention by an intramedullary distraction pin and is fitted into the central bores. After the desired lengthening of the bone by means of callus distraction, i.e. formation of new bone tissue, such intramedullary pins in most cases have to be removed again and replaced by a stablilizer, since the intramedullary pins do not have sufficient stability for permanent implantation of the prosthesis.

Moreover, DE 199 06 423 A1 discloses an active intramedullary pin which is used for distraction of bone parts and which consists of two elements, prostheses or the like that are movable relative to each other and have at least one electrically operated drive element. The electrical energy needed for the drive element is delivered to the intramedullary pin via at least one releasable plug element. Should the intramedullary pin be integrated in the prosthesis, it is of particular advantage in this invention that, after the desired distraction has been completed, only the electric plug connector has to be removed, not the entire intramedullary pin. However, there is still the problem in this invention that, because of the predefined length, a not inconsiderable portion of healthy bone has to be removed for introducing the prosthesis.

The disadvantage of the identified prior art is, on the one hand, the relatively large diameter of growing prostheses that comprise planetary roller drives. Such prosthesis models are suitable only to a limited extent in the medical treatment of hip joints and knee joints that are to be replaced in children and adolescents. The long minimum length of the prosthesis, which is predefined by the relatively long length of the drive, is also a considerable disadvantage since, in children with smaller bones, the long and predefined length of the prosthesis means that more bone than necessary has to be removed in order to create the space for receiving the prosthesis that is to be implanted.

It is therefore the object of the present invention to provide a growing prosthesis which diverges from the principle of callus distraction and which at the same time has a reduced prosthesis length and a reduced prosthesis diameter, so as to permit easier use of such prostheses in children and adolescents or in persons of small stature.

SUMMARY OF THE INVENTION

The foregoing object is achieved by a growing prosthesis comprising a prosthesis stem, a joint replacement part, a stem-anchoring element, and an element with corresponding drive provided for the lengthening of the growing prosthesis.

The element of the growing prosthesis designated as the joint replacement part is of such a shape and geometry that it is similar to a joint to be replaced, e.g. knee, hip, etc., that is to say represents a joint replacement part. This element is typically made of implant-grade steel or similarly known materials.

The joint replacement part is in this case fitted in the prosthesis stem, and these are secured against rotation relative to each other.

The stem-anchoring element represents an element of the growing prosthesis lying opposite the joint replacement part and prosthesis stem and is introduced into and fixed in the medullary cavity of the bone. After the removal of a hip joint or knee joint because of a bone tumor, it may happen that no shortening of the leg is observed at first, as a result of which a distraction of the bone is not necessary initially. In children and adolescents, however, the natural growth of the bone means that differences in leg length are seen after just a very short period of time and have to be treated medically as a result.

The growing prosthesis therefore has an element with drive that serves for the lengthening of the entire prosthesis and that is able to compensate for postoperative differences in the length of the limbs.

According to the invention, the element provided for the lengthening of the growing prosthesis is a spindle element arranged in the stem-anchoring element.

As a result of this arrangement, the length and the diameter of the growing prosthesis are reduced by a considerable amount and are therefore particularly suitable in the treatment of children and adolescents with smaller bones.

The growing prosthesis is also of modular construction. That is to say, the individual component parts of the prosthesis can be selected and combined according to the anatomical circumstances. Thus, the individual elements of the prosthesis can be interchanged and used depending on the diameter and length of the existing bones.

By virtue of the modular construction of the growing prosthesis, it is also possible to easily remove the spindle element and the drive from the prosthesis after completion of the lengthening process.

It is also possible for the prosthesis, fitted after removal of the tumor, to be implanted initially without the drive and for the latter to be fitted only after chemotherapy has been successfully completed.

To be able to fit the spindle element in the stem-anchoring element, the stem-anchoring element has a bore, specifically a bore corresponding to the length and nature of the spindle element, and the bore extends almost completely along the length of the stem-anchoring element.

An inner thread for receiving and supporting the spindle element can be arranged directly in the stem-anchoring element, in a screw for connection of stem-anchoring element and prosthesis, or in a threaded element inserted with a form fit.

The diameter chosen for the bore of the stem-anchoring element is such as to be able to receive a spindle element that is sufficiently large in respect of the force applied for the lengthening of the growing prosthesis, without any significant reduction occurring in the strength of the stem-anchoring element.

In the device according to the invention, the outer thread of the spindle element corresponds in terms of thread pitch and thread dimension to that of the thread arranged in the stem-anchoring element. It is designed in such a way as to ensure a desired continuity of movement and the necessary freedom from play, and to allow an adopted path of travel to be reliably maintained.

The drive of the spindle element is expediently placed in the joint replacement part. The space-saving arrangement of the drive can be achieved by means of a suitably large bore at the end of the joint replacement part, without having to accept any significant reduction in stability, especially since the material of the bone prosthesis, as has already been mentioned, is implant-grade steel, ceramic or similar materials.

The drive of the spindle element preferably comprises a motor with step-down gear.

It is conceivable, in this connection, for the drive to be embodied as a piezoelectric actuator, as a shape-memory actuator, or as an electromagnetic or magnetic drive. However, the invention is not limited to these.

In a preferred embodiment of the invention, a mating piece provided for the spindle, and in the form of a threaded element having a through-hole with inner thread, is introduced with a form fit into the bore at the end of the stem-anchoring element.

The threaded element in this case serves as a supporting means for the spindle element.

The threaded element can in this case be made of implant-grade steel, ceramic or plastic. These materials ensure the necessary stability and strength of the threaded element.

The threaded element preferably has an outer contour securing it against rotation. The threaded element thus forms a form-fit plug connection, which ensures simple withdrawal and introduction of the spindle element, by means of the threaded element being mounted onto the spindle element, prior to the insertion of the latter, and then being able to be locked with a form fit in the stem-anchoring part without laborious screwing in.

By virtue of the plug connection and the modular construction of the growing prosthesis, the drive with spindle element can be removed separately after complete lengthening of the prosthesis.

The drive can therefore also be introduced into the growing prosthesis a short time after the actual implantation of the growing prosthesis, provided that the medical indication for lengthening is made only at a later time.

The growing prosthesis is especially suitable in the medical treatment of bone tumors in young children and adolescent patients whose phase of growth has not yet been completed and who have smaller bones and therefore require prostheses that are adapted specifically to their needs. In many cases, the occurrence of bone tumors leads to amputation of the near hip joint, knee joint, elbow joint, wrist or shoulder joint (etc.). The missing joint is replaced by the joint replacement part, and the lengthenable structure in the form of a spindle element ensures adaptation to the difference in the length of the limbs that occurs on account of the natural and as yet incomplete bone growth. Because the prosthesis is narrow and short, a smaller amount of healthy bone substance has to be removed upon implantation of the growing prosthesis.

A further advantage resulting from the small resection length is the favorable ratio of bone to prosthesis, which results in greater stability.

In another embodiment, it is conceivable that the stem-anchoring element and the prosthesis stem are formed in one piece. In such a case, no screw is needed for connecting the two elements. The threaded element can also be omitted in such an embodiment. The thread corresponding to the spindle element can then be arranged directly in the stem-anchoring element for example.

However, it is also conceivable for the growing prosthesis to be used in adult patients who are being treated as a result of congenital, pathological or accident-related differences in leg length. The compact and scaled-down design of the prosthesis is also easier to implant in such applications, and removal of the drive or of the spindle element can be carried out more easily.

BRIEF DESCRIPTION OF THE DRAWINGS

The invention is explained in more detail below on the basis of an illustrative embodiment and with reference to figures, in which.

DETAILED DESCRIPTION

Figure 1:
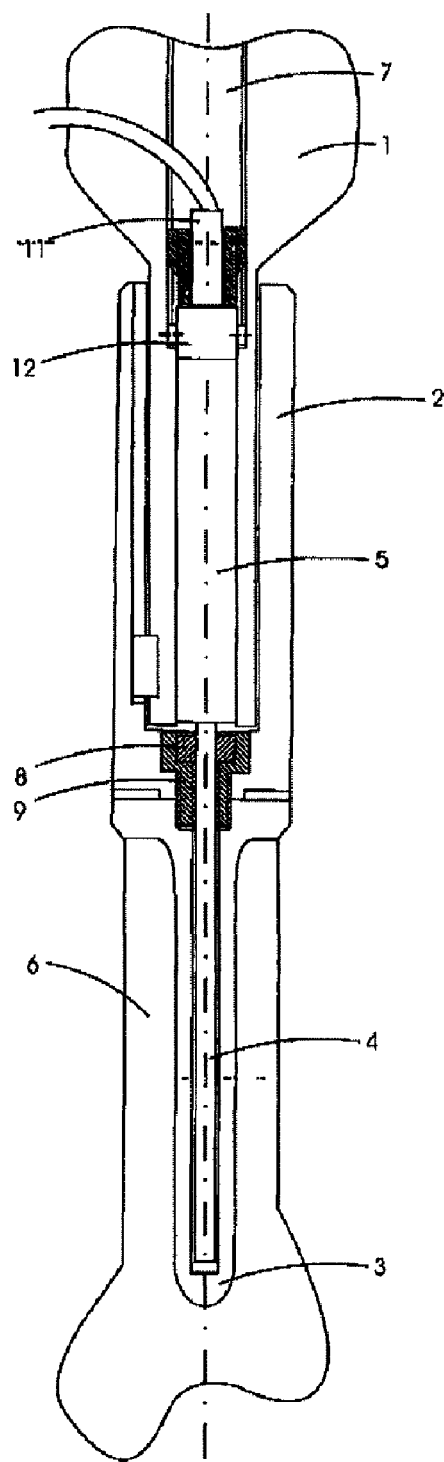
FIG. 1 shows a schematic representation of the growing prosthesis according to the invention.

As is illustrated in FIG. 1, the growing prosthesis is composed of the joint replacement part 1, the prosthesis stem 2, the stem-anchoring element 3, the spindle element 4, and the drive 5 belonging to the spindle element 4.

The joint replacement part 1 is in this case arranged in the prosthesis stem 2 open at the top.

The joint replacement part 1 replaces at least some of the removed knee joint or hip joint, is made of implant-grade steel, ceramic or similar materials, and receives the drive 5 of the spindle element 4 in a dedicated bore 7. The sizes of the bore 7 and of the drive 5 are in this case chosen in such a way that there is no significant reduction in the stability of the prosthesis.

The spindle element 4, in the state of insertion, is located in a bore formed in the stem-anchoring element 3. The spindle element 4 in this case fills a very large part of the length of the stem-anchoring element 3, which is fixed in the bone 6 of the patient. This type of construction permits a considerable reduction in the overall length of the growing prosthesis and in the diameter in the area of the drive.

The outer thread of the spindle element 4 corresponds in terms of thread pitch and thread size to the thread 10 of the threaded element 8, serves to support the spindle element 4 and to convert the rotary movement into a linear movement, ensures the necessary freedom from play, and reliably maintains an adopted path of travel by means of a suitable spindle pitch.

Joint replacement part 1 and prosthesis stem 2 are secured against rotation relative to each other. The drive 5 must be mounted in the joint replacement part axially and in a manner secure against rotation.

Figure 2:
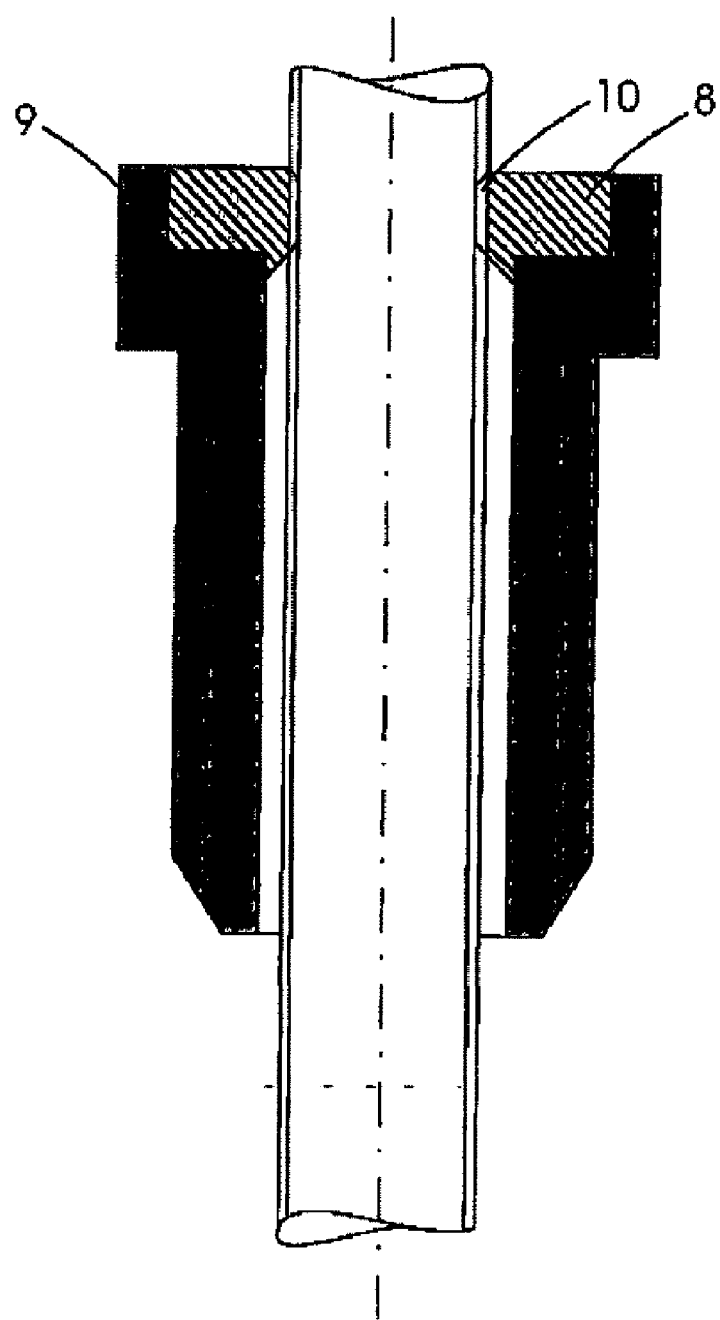
FIG. 2 shows a detail of the screw with threaded element.

A screw 9 with threaded element 8 is introduced into a bore at the end of the stem-anchoring element 3 and of the prosthesis stem 2 and serves as a mating piece for the spindle element 4 (FIG. 2).

Figure 3:
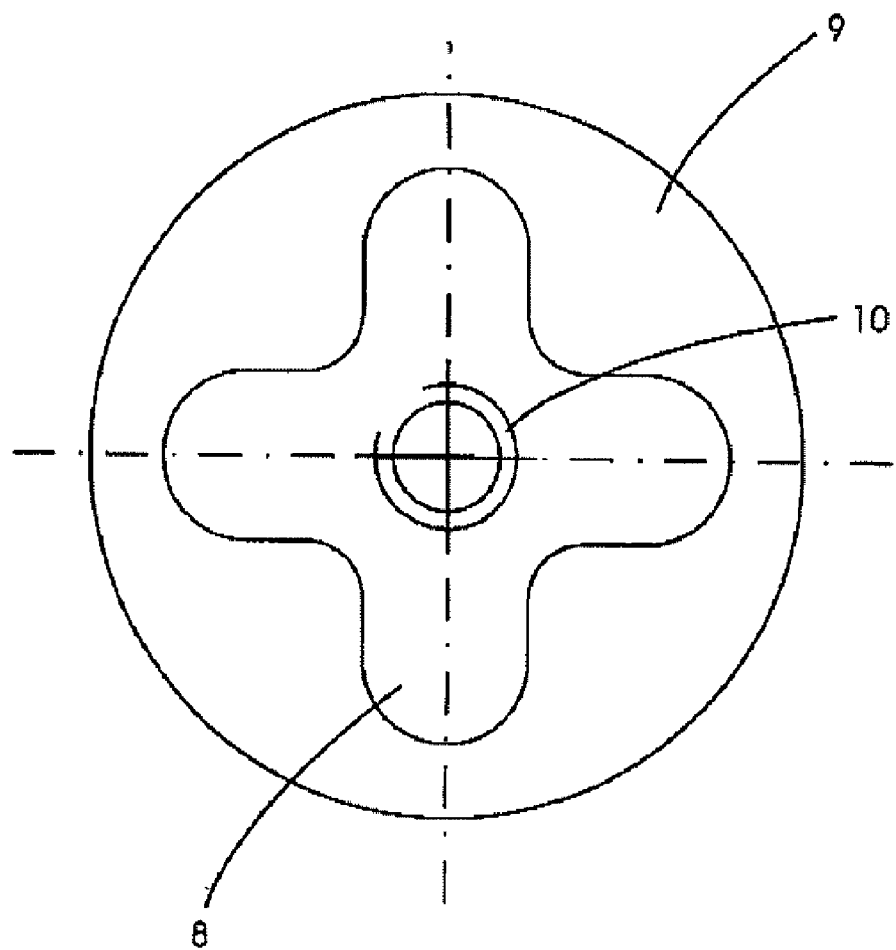
FIG. 3 shows a plan view of the screw with threaded element.

As is shown in FIG. 3, the screw 9 has a cloverleaf-shaped recess or depression, into which the threaded element 8 with thread 10 is inserted with a form fit, and serves to secure the spindle element 4 relative to the stem-anchoring element 3.

With this form-fit plug connection, it is possible to ensure simple withdrawal and introduction of the spindle since, by means of the threaded element 8 being turned onto the spindle element 4, prior to the insertion of the latter, and then being able to be locked with a form fit in the stem-anchoring part 3 without laborious turning-in of the spindle element 4. Withdrawal takes place in the same way.

Thus, the spindle element 4 and the drive 5, which in the example shown is designed in the form of a motor 11 with a gear 12, can be easily removed through the bore 7 of the joint replacement part 1, if this is no longer needed for further treatment. The achieved distraction length can be maintained by insertion of a dummy/spacer.

The invention claimed is:

1. Growing prosthesis comprising a joint replacement part (1), a prosthesis stem (2), a stem-anchoring element (3), and a drive (5) including a spindle element (4) for lengthening of the growing prosthesis, wherein the joint replacement part (1) has an end with a shape and geometry similar to a joint to be replaced, an opposite cylindrical end, and an inner central bore formed therein, wherein the prosthesis stem (2) is a substantially cylindrical structure having said stem-anchoring element (3) attached at one end thereof and an opposite open end having an inner central bore formed therein, wherein the cylindrical end of the joint replacement part (1) is telescopically fitted within the inner central bore of the prosthesis stem (2), wherein said spindle element (4) is arranged in the stem-anchoring element (3), the drive (5) of the spindle element (4) is integrated within the inner central bore of the joint replacement part (1), wherein a screw (9) with a threaded element (8) is introduced into a bore at one end of the stem-anchoring element (3) and serves as a mating piece for the spindle element (4), the threaded element (8) having a through-hole with an inner thread (10) therein, wherein the screw (9) has a cloverleaf-shaped recess or depression into which the threaded element (8) is inserted with a form fit, wherein the threaded element (8) is connected with a form fit to the stem-anchoring element (3), and wherein the threaded element (8) serves as a fixing means for the spindle element (4) against the stem-anchoring element (3), wherein the form fit connection ensures simple removal or insertion of the spindle, and wherein the prosthesis has a reduced prosthesis length and a reduced prosthesis diameter so as to permit easier use of such prostheses in children and adolescents or in persons of small stature.

2. Growing prosthesis according to claim 1, wherein the growing prosthesis is of modular construction.

3. Growing prosthesis according to claim 1, wherein the stem-anchoring element (3) has a bore for receiving the spindle element (4).

4. Growing prosthesis according to claim 3, wherein the bore of the stem-anchoring element (3) is provided with a diameter which is able to receive the spindle element (4) and is sufficiently large with respect to a force applied for the lengthening of the growing prosthesis that no significant reduction occurs in strength of the stem-anchoring element.

5. Growing prosthesis according to claim 1, wherein the drive (5) of the spindle element (4) comprises a motor (ii) with gear (12).

6. Growing prosthesis according to claim 1, wherein the drive (5) of the spindle element (4) comprises a piezoelectric motor.

7. Growing prosthesis according to claim 1, wherein the drive (5) of the spindle element (4) comprises a shape-memory actuator.

8. Growing prosthesis according to claim 1, wherein the drive (5) of the spindle element (4) is removed or installed during the implantation period.

* * * * *